United States Patent [19]
Arnaud et al.

[11] Patent Number: 4,874,952
[45] Date of Patent: Oct. 17, 1989

[54] DEVICE FOR ACCELERATED PHOTO-AGING OF MATERIALS CONTAINING POLYMERS

[75] Inventors: Rene Arnaud, Clermont-Ferrand; Jean-Luc Gardette, Aubiere; Jacques Lamaire, Beaumont, all of France

[73] Assignee: Universite De Clermont II, Laboratoire De Photochimie, Aubiere, France

[21] Appl. No.: 187,367

[22] Filed: Apr. 28, 1988

[30] Foreign Application Priority Data

Apr. 28, 1987 [FR] France ............................ 87 06216

[51] Int. Cl.$^4$ ............................................. G01N 17/00
[52] U.S. Cl. ............................... 250/455.1; 250/453.1; 250/492.1; 73/865.6
[58] Field of Search ............... 250/453.1, 454.1, 455.1, 250/492.1; 73/865.6

[56] References Cited

U.S. PATENT DOCUMENTS

| | | | |
|---|---|---|---|
| 3,664,188 | 5/1972 | Kockott | 250/453.1 |
| 3,886,791 | 6/1975 | Grossman | 73/865.6 |
| 4,011,456 | 3/1977 | Bredewater et al. | 250/453.1 |
| 4,544,995 | 10/1985 | Suga | 73/865.6 |
| 4,627,287 | 12/1986 | Suga | 73/865.6 |
| 4,760,748 | 8/1988 | Katayanagi et al. | 73/865.6 |

Primary Examiner—Janice A. Howell
Assistant Examiner—John A. Miller
Attorney, Agent, or Firm—Oblon, Spivak, McClelland, Maier & Neustadt

[57] ABSTRACT

A device for the accelerated photo-aging of materials containing polymers, enables samples of the materials to be submitted to the simultaneous action of ultraviolet radiation, temperature and oxygen in an aqueous or gaseous phase with a view to being able to analyze and interpret the phenomena of photodegradation. An external enclosure contains at least four sources of ultraviolet radiation evenly distributed at its periphery and at least one cylindrical wall which is transparent to radiations of at least equal to 295±5 nm and which is coaxial to the external enclosure. A sample holder is arranged coaxially to the vat and moved uniformly in rotation around its vertical axis. Devices are also provided for circulating an aqueous phase inside the cylindrical vat, for regulation of the temperature of the aqueous phase, for ensuring the saturation in oxygen of the aqueous phase, for circulating a gaseous phase inside the external enclosure, and for regulating the temperature of the exposed samples.

12 Claims, 1 Drawing Sheet

DEVICE FOR ACCELERATED PHOTO-AGING OF MATERIALS CONTAINING POLYMERS

BACKGROUND OF THE INVENTION

1. Field of the Invention

The invention relates to a device for the accelerated photo-aging of materials containing polymers, which device enables measurement of their capability to resist the simultaneous action of ultraviolet radiation, temperature and oxygen in an aqueous or gaseous phase in order to analyze with a view to better understanding the phenomena of photodegradation and to determining the correlations between the life spans of said materials under accelerated photo-aging and under climatic aging.

2. Background of the Related Art

It has been known for a long time that polymers exposed to natural climatic conditions undergo over time an alteration in their chemical nature which is manifested, for example, by a modification in their surface appearance (discoloration, loss of brilliance, becoming powdery, etc.) most often accompanied over time by a degradation of their mechanical characteristics (resistance to traction, stretching, shock resistance, rigidity).

To better comprehend the overall phenomena occurring during exposure of said polymers to natural climatic conditions, numerous simulation devices have been proposed to enable the reproduction in an accelerated manner of the effects noted naturally on said materials.

An accelerated photo-aging device for polymers is known from French Patent No. 2 430 609, which comprises chamber in which a single lamp emits a narrow parallel beam of ultraviolet radiation which irradiates a group of test pieces mounted on a sample holder, which group is reciprocally moved in translation in a plane perpendicular to the axis of the beam. The temperature of the chamber is regulated so as to maintain constant the temperature of the test pieces, by means of temperature sensors in direct contact with said test pieces.

Such a device has disadvantages which are bothersome in use. Firstly, the polymer test pieces are submitted only to localized and discontinuous exposure to ultraviolet radiation due to the reciprocating movement of the sample holder. In addition, due to its construction, this device allows the simultaneous irradiation of only a small number of test pieces. Finally, such a device enables irradiation only in a dry atmosphere and, consequently, does not enable the study of the phenomena of photodegradation in the presence of an aqueous phase.

However, the accelerated photo-aging of polymers must necessarily be representative of the most extreme climatic phenomena, that is, not only the physical aggressions due to natural light and variations in temperature must be taken into account, but also the chemical aggressions due to the presence of an aqueous medium and/or oxygen such as occurs when the materials produced from polymers are used in direct contact with these natural elements.

Devices enabling a more complete climatic simulation by means of exposure in a damp medium have been proposed in the specialized literature dealing with the accelerated photo-aging of polymers.

A first type of device comprises an enclosure in which is placed a radiation chamber provided at its central part with three 4.5 kW Xenon lamps arranged in a triangle, with each lamp being provided with selective reflecting flat metal mirrors for ultraviolet light, around which are arranged two coaxial quartz cylinders, comprising an annular volume in which a cooling fluid circulates. Placed between the enclosure and the ultraviolet radiation chamber there is a cylindrically shaped sample holder moved in continuous or alternating rotation. In addition, the device is provided in the upper part of the enclosure with one to three sprinkler ramps fitted with three nozzles enabling the creation of a damp internal atmosphere and/or a sprinkling of water onto the test pieces. Finally, the device contains means enabling the temperature within the enclosure to be regulated by means of the continuous measurement of a black body located therein and to automatically adjust the test piece sprinkling cycles. Such a device is known by the trade name of XENOTEST 1 200 HERAEUS.

Another type of device sold under the trademark HERAEUS XENOTEST 250 T, provided with means for the thermal regulation of the enclosure and means for spraying water and adjusting the cycles of the spraying according to the preceding technique, is provided with a parabola-shaped reflector with a vertical axis, whose source is provided with a low pressure Xenon burner fitted with a filter, with the test pieces being arranged flat on the horizontal floor of the enclosure which thus acts as the sample holder.

In use, both of these devices have major disadvantages.

In order for the phenomenon of degradation of polymers subjected to ultraviolet irradiation to be significant and reproducible, it is first of all necessary for the actual temperature of the samples to be maintained constant throughout the tests and at a known value. However, in the two above-identified devices, the temperature of the polymer samples is not measured in a precise manner because, in each device, the temperature of the enclosure containing the samples is regulated via the measurement of the temperature of a black body placed in said enclosure, which temperature, according to the radiation properties of said body, is always higher than that of the samples. In addition, in the second device, resistance probes are arranged on a small rule placed in direct contact with the sample holder so as to measure, as far as possible, the temperature of the samples. However, because of the differences in temperature due to the imperfection of the thermal contacts between the resistance probes, the sample holder floor and the polymer samples arranged on said floor, the temperature measured by the resistance probes is different from that of the exposed materials.

In addition, the samples of polymer used in the second device are maintained in a fixed position. Since the radiation emitted cannot have a perfectly homogeneous distribution over the entire volume of the irradiation chamber, the result is that the incident light intensity received by the samples during the total time of their irradiation cannot be the same from one sample to another and that heterogeneous distribution of said intensity can cause inaccurate aging test results.

Finally, a more specific device has been proposed which consists of a parallelepipedal enclosure on which is placed a prism-shaped assembly provided with eight fluorescent tubes producing ultraviolet radiation placed horizontally, four by four, along two concurrent surfaces of the prism-shaped assembly. The samples to be irradiated are then arranged between the tubes and the two above-identified concurrent surfaces. The space defined by said concurrent surfaces and the samples enables a natural circulation of ambient air for cooling.

In its lower part, this device is also provided with a water vat for the generation of water vapor. The difference in temperature existing between the water vapor and the internal irradiated surface of the samples cooled at their external surface due to the circulation of ambient air is sufficient to cause condensation of that water vapor coming into contact with said internal surface. The thermal gradient which is established within the thickness of the sample does not enable the temperature of the irradiated material to be determined. In addition, like the second device described above, the samples placed along the concurrent surfaces of the enclosure are maintained in a fixed position throughout the entire time of the experiments and cannot therefore receive an equal amount of radiation from one sample to another.

Finally, this device is provided with light sources emitting energy in the range of 270 to 350 nm which includes a photon-rich zone (between 270 and 300 nm) which does not exist in the solar spectrum. The short wavelengths can create unrepresentative phenomena of natural aging in the accelerated laboratory photo-aging tests, such as accelerated photopassivation or photodegradation phenomena.

While the three devices described offer the possibility of enabling the study of photo-aging of samples of polymers subjected to the action of running water or water vapor which condenses directly on contact therewith and while they also enable the simultaneous reproduction of certain water washing effects (physical taking up and/or dissolving of additives or chemical photodegradation products having migrated to the surface of the test pieces) and certain mechanical effects, they do not enable the reproduction and understanding of the chemical role of water during the irradiation nor even its possible role as an extraction solvent. Likewise, it has been noted that, under the photo-oxidizing action of functional organic groups which are particularly sensitive to the action of water and by a hydrolysis reaction, certain materials generate a breakage of the molecular chains accompanied by a degradation of the mechanical properties of said material.

To be significant, a simulation of the effect of the water must be characterized by the presence of a film of water maintained in direct and permanent contact with the polymer throughout the irradiation, with the oxygen concentration of said water being controlled and maintained at a constant value. However, the devices described above do not enable the presence of a film of water of a given thickness over the entire surface of the irradiated test piece to be permanently ensured.

Thus, a test piece produced using a thin strip of very hygroscopic polyamide, subjected in a sequential manner to sprinkling by spraying in a photo-aging enclosure brought to a temperature of between 40 and 70° C. has a dry surface a few minutes after the end of the sprinkling.

SUMMARY OF THE INVENTION

In view of the above-identified disadvantages, the present invention provides an accelerated photo-aging device for materials containing polymers, enabling samples of said materials to be subjected to the simultaneous action of ultraviolet radiation, temperature and oxygen in an aqueous or gaseous phase for the purpose of being able to analyze and interpret the phenomena of photodegradation.

The device in accordance with the invention includes an external enclosure which is polyhedral or possibly cylindrical in shape and having a vertical axis of symmetry, at least four sources of ultraviolet radiation evenly distributed at the periphery of the external enclosure and each emitting a beam of radiation in a selected wavelength range, at least one cylindrical wall which is transparent to radiation having a wavelength at least equal to 295±5 nm and which is coaxial to the external enclosure, a sample holder arranged coaxially to the vat and moved uniformly in rotation around its vertical axis, means circulating an aqueous phase inside the cylindrical wall, means regulating the temperature of the aqueous phase, means for saturating in oxygen the aqueous phase, means, for circulating a gaseous phase inside the external enclosure, and means for regulating the temperature of the exposed samples.

To enable the carrying out of accelerated photodegradation tests on samples of material containing polymers, which tests must be representative of natural photo-aging, the device in accordance with the invention comprises, as has been indicated, at least one cylindrical wall which is transparent to radiation having a wavelength at least equal to 295±5 nm, said wall being coaxial to the external enclosure of the device.

For the case where the samples are irradiated while they are immersed in an aqueous phase, the device is provided with at least one and preferably two parallel cylindrical walls constituting the lateral walls of a crown-shaped vat which is closed in its lower part and open in its upper part, the hollow central part of which permits the axial placing of the sample holder. The annular space in which the samples suspended on the sample holder are placed has a constant cross-section and enabled a volume of liquid with a controlled thickness to be maintained continuously in contact with the sample which can be partially and/or totally immersed in said liquid.

The distance between the two parallel cylindrical walls is such that it guarantees the existence of a film of water on the samples. This distance is between 5 and 50 and preferably between 10 and 30 millimeters.

These walls are generally produced of an optical material such as borosilicate glass which is transparent to ultraviolet radiations having wavelengths at least equal to 295±5 mn.

In order that the samples undergo a very homogeneous irradiation, the sample holder is moved in a uniform rotation movement at a slow speed so that each sample moving evenly throughout the entire irradiation on the perimeter of the cylindrical wall receives a same amount of light flux.

The device in accordance with the invention is also provided with a means placed outside of the enclosure which continuously circulates the aqueous phase in the annular space of the crown shaped vat. The temperature of said aqueous phase is regulated to a value selected by the skilled artisan using any known means such as a heat exchange or thermostat. This temperature thus enables the temperature of the samples to be fixed and controlled in a very precise manner.

During the irradiation, the oxygen present in the aqueous phase is consumed in whole or in part by a photochemical reaction on contact with the polymer. This oxygen must be renewed in such a manner that its concentration in the aqueous phase in contact with the samples remains approximately constant over time. A suitable means, such as for example one providing energetic stirring or blowing of air or oxygen, placed outside the enclosure, enables the oxygen, placed outside the enclosure, enables the oxygen content of the circulating aqueous phase to be maintained at its saturation point.

The sources emitting ultraviolet radiation are arranged in an even manner on the periphery of the external enclosure. Said sources are preferably average pressure mercury vapor arc lamps emitting a photon-rich light with wavelengths of between 290 and 450 nm. The shortest distance between the burner of one lamp and a sample can be selected in the range of 7 to 50 centimeters, and preferably close to 20 centimeters. This preferred range is adopted by the skilled artisan with a view to increasing the efficiency of the ultraviolet radiation and thus shortening the length of exposure time of the samples by increasing the photodegradation acceleration factor.

The number of sources emitting ultraviolet radiation is generally at least four. However, it may be more in order to provide an increase in the light flux and, consequently, to cause an increase in the speed of photo-oxidation. Thus, the increase in the number of emitting sources, for example the increase from four to six emitting sources, enables the acceleration factor of the aging device to be increased, especially when the permitted temperature is greater.

The temperature existing inside the external enclosure, that is in the gaseous phase, is controlled and regulated in relation to an average reference value, for example that of a temperature probe in contact with a reference sample which is not immersed in the aqueous phase and is representative of all the simultaneously irradiated samples. For this purpose, the device in accordance with the invention contains at least two and preferably at least three ventilators for the introduction of air and at least one ventilator for the removal of air, which are provided on the walls of the external enclosure. The starting up and stopping of these ventilators is controlled by any means known to the skilled artisan, such as a regulator comparing the measured temperature with that of a reference temperature. It is thus possible to maintain the temperature of the gaseous phase contained in the enclosure at the reference value by introducing into the enclosure fresh air taken from the outside atmosphere and, at the same time, removing the hot air.

The temperature of the samples in the gaseous phase which are being exposed is thus controlled and regulated using this reference value by means of said temperature probe. Where the samples are immersed in the aqueous phase, their temperature is controlled and regulated using a reference value by the temperature of the circulating water.

The sample holder is composed of three main components, which are a shaft, a means for driving in rotation and at least one plate. The shaft is positioned vertically and coaxially to the axis of the vat. It is provided at its lower end with a means for driving it in rotation and at it supper end with a circular plate which has a diameter substantially equal to that of the crown. Means for fixing the samples are arranged at regular intervals on the periphery of the circular plate. Each sample is thus suspended from the plate in a vertical position, with its lower end able to remain free.

In accordance with an alternative embodiment, weights having a given value can be fixed on the lower part of each sample so as to maintain them under controlled traction throughout the irradiation time. It is thus possible to carry out the photo-aging study of polymers under traction, so as to cause premature degradation of the mechanical properties of the samples irradiated in this manner.

In accordance with another alternative, and more generally in the case of exposure in the aqueous phase, each sample can be inserted into a suitable support suspended on the circular plate.

In accordance with another embodiment and where the irradiation is carried out in the gaseous phase, the sample holder can be provided with a second plate located between the driving means and the upper plate and capable of sliding on the shaft.

The speed of rotation of the sample holder is generally selected in the range of 1 to 8 and preferably 3 to 5 revolutions per minute.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
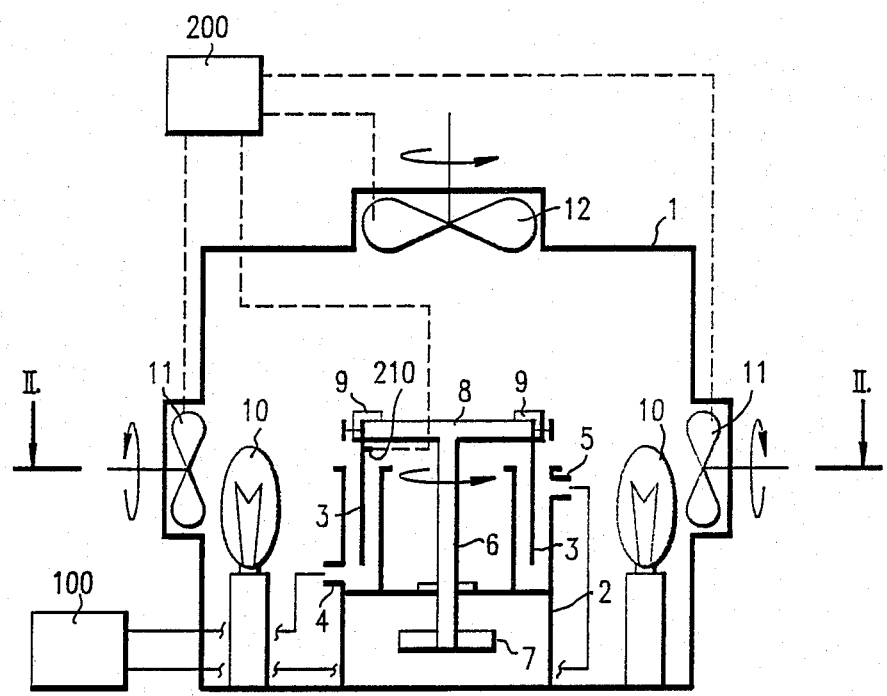
FIG. 1 is a schematic elevation view of a device according to the invention.
Figure 2:
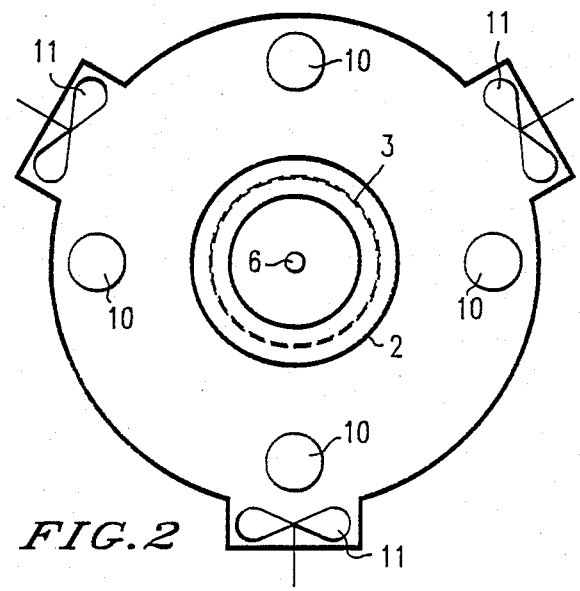
FIG. 2 is a cross-section of the device along line II—II in FIG. 1.

The device shown in FIGS. 1 and 2 includes an external envelope (1) which, as shown in FIG. 2, has a cylindrical shape but which in accordance with the invention may have any other shape comprising a body of revolution around a vertical axis, such as a polyhedron.

A doubled-walled vat (2) is positioned in the enclosure and is made of a material transparent to radiation having a wavelength of at least $295 \pm 5$ nm. An aqueous phase circulates in the annular space defined by the two cylindrical walls of the vat. The upper end of the annular space is open so as to enable the insertion therein and the rotation of the samples (3). Small tubes (4) and (5) connected vat (2) are in turn connected to suitable means (100) located outside the enclosure, for example means including a pump, a heat exchanger and an oxygen generator, which continuously circulates the liquid phase in the annular space of the vat (2), while maintaining a temperature and an oxygen concentration which are regulated to desired values.

A sample holder is composed of a shaft (6) provided at its lower part with a means (7) such as a pulley enabling it to be driven in rotation. The upper part of shaft (6) is connected to a plate (8) having jaws (9) on its upper part on which sample holders are fixed and into which the samples (3) are inserted.

An assembly of four average pressure mercury vapor lamps (10) emitting photon-rich ultraviolet radiation having wavelengths at least equal to $295 \pm 5$ are evenly distributed around the vat.

An assembly of three ventilators (11) driven so as to provide the introduction of fresh air are arranged on the lateral walls of the enclosure. A fourth ventilation (12), driven so as to provide the removal of the hot air, is placed on the cover of the enclosure. The starting up and the stopping of these ventilators is controlled by an electronic temperature regulator (200) in response to the measurement of the temperature of a reference sample which is not immersed in the liquid phase, the measurement being made by means of a thermometric sensor (210) such as a platinum probe or thermocouple.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A device for the accelerated photo-aging of materials containing polymers, for enabling samples of said materials to be submitted to the simultaneous action of ultraviolet radiation, temperature and oxygen in an aqueous or gaseous phase, with a view toward analyzing and interpreting the phenomena of photodegradation, comprising:
   (a) an external enclosure having a vertical axis of symmetry,
   (b) at least four sources of ultraviolet radiation evenly distributed about said axis of symmetry in said external enclosure for emitting beams of radiation in a selected wavelength range,
   (c) a vat defining an annular space and having at least one cylindrical wall which is transparent to radiation having a wavelength at least equal to 295±5 nm and which is coaxial with the external enclosure,
   (d) means for circulating a liquid aqueous phase within said vat,
   (e) a sample holder arranged coaxial with said transparent cylindrical wall and including means for holding a sample immersed in the liquid aqueous phase within said vat,
   (f) means for rotating said sample holder around said axis of symmetry, wherein said sample rotates in the liquid aqueous phase,
   (g) means for regulating the temperature of the aqueous phase,
   (h) means providing oxygen saturation of the circulating aqueous phase,
   (i) means for circulating a gaseous phase inside the external enclosure, and
   (j) means for regulating the means for circulating the gaseous phase such that the temperature of the exposed samples is regulated.

2. The device for accelerated photo-aging in accordance with claim 1, wherein the sources of ultraviolet radiation are average pressure mercury vapor lamps emitting radiations with wavelengths of between 290 and 450 nm.

3. The device for accelerated photo-aging in accordance with claim 2, wherein said at least one cylindrical wall comprises two parallel cylindrical walls constituting the lateral walls of said vat, said vat being crown-shaped and having a closed lower part and an open upper part, and means positioned within an inner one of said cylindrical walls for supporting said sample holder, wherein said walls are transparent to radiation having a wavelength at least equal to 295±5 nm.

4. The device for accelerated photo-aging in accordance with claim 3, wherein the distance between the two parallel transparent cylindrical walls of the vat defining the annular space is between 5 and 50 millimeters.

5. The device for accelerated photo-aging in accordance with claim 3, wherein the cylindrical walls which are transparent to radiations of at least equal to 295±5 nm are made of borosilicate glass.

6. The device for accelerated photo-aging in accordance with claim 3, wherein the sample holder comprises a shaft which is coaxial to the vat, means positioned at the lower part of said shaft for driving said shaft in rotation and a plate at an upper end of said shaft on which the samples are suspended.

7. A device for accelerated photo-aging in accordance with claim 1, including means for rotating the sample holder at a speed of between 1 and 8 revolutions per minute.

8. The device for accelerated photo-aging in accordance with claim 1, wherein the shortest distance between one of said sources of radiation and the sample is from 7 to 50 centimeters.

9. The device for accelerated photo-aging in accordance with claim 8, wherein the shortest distance between one of said sources of radiation and the sample is 20 centimeters.

10. The device for accelerated photo-aging in accordance with claim 1, wherein said means for regulating the circulation of the gaseous phase comprises a temperature probe in contact with a reference sample being irradiated which is not immersed in the aqueous phase and for controlling said means for circulating the gaseous phase as a function of a difference between a temperature measured by said probe and a reference value.

11. The device for accelerated photo-aging in accordance with claim 1 wherein the means for circulating the gaseous phase comprise at least two ventilator means for the introduction of air into said external enclosure and at least one ventilator means for the removal of air from said external enclosure.

12. The device for accelerated photo-aging in accordance with claim 1, wherein said means for regulating the aqueous phase includes means for comparing the temperature of said aqueous phase with a reference value.

* * * * *